United States Patent
Vito

(10) Patent No.: US 6,322,553 B1
(45) Date of Patent: *Nov. 27, 2001

(54) AUTOLOGOUS VASCULAR GRAFTS CREATED BY VESSEL DISTENSION

(75) Inventor: Raymond P. Vito, Atlanta, GA (US)

(73) Assignee: Georgia Tech Research Corporation, Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,095

(22) Filed: May 28, 1999

Related U.S. Application Data

(60) Provisional application No. 60/087,027, filed on May 28, 1998.

(51) Int. Cl.[7] ............................... A61B 17/00

(52) U.S. Cl. ................ 606/1; 606/159; 623/903; 600/36

(58) Field of Search ............... 606/1, 159, 194; 600/36; 623/1.1, 903

(56) References Cited

U.S. PATENT DOCUMENTS

| | | | |
|---|---|---|---|
| 5,078,726 | * | 1/1992 | Kreamer ............... 606/194 |
| 5,344,425 | | 9/1994 | Sawyer . |
| 5,549,664 | | 8/1996 | Hirata et al. . |
| 5,702,419 | | 12/1997 | Berry et al. . |
| 5,713,917 | | 2/1998 | Leonhardt et al. . |
| 5,879,875 | | 3/1999 | Wiggins et al. . |
| 5,888,720 | | 3/1999 | Mitrani . |
| 5,899,936 | | 5/1999 | Goldstein . |

OTHER PUBLICATIONS

Birukov, et al., "Stretch affects phenotype and proliferation of vascular smooth muscle cells," *Mol Cell Biochem.* 144(2):131–39 (1995).

Conklin, B. *Viability of Porcine Common Carotid Arteries in a Novel Organ Culture System MS Thesis*, Georgia Institute of Technology, 1997.

Costa, et al., "Increased elastin synthesis by cultured bovine aortic smooth muscle cells subjected to repetitive mechanical stretching," *FASEB J.* 5:A1609–7191 (1991).

(List continued on next page.)

*Primary Examiner*—Linda C. M. Dvorak
*Assistant Examiner*—Jocelyn Debra Ram
(74) *Attorney, Agent, or Firm*—Sutherland Asbill & Brennan, LLP

(57) ABSTRACT

A method is provided for forming an autologous graft by distending a donor blood vessel and harvesting the distended portion of the vessel. Also provided is a device for in vivo or in vitro vessel distension. Typically the device is implanted, for example using endoscopic techniques, in a patient sometime prior to another surgery on that patient which includes implanting a vascular graft. The device includes a stretching mechanism which is attached to a donor blood vessel, means for operating the stretching mechanism to cause the vessel to distend, and a controller, preferably externally located, for controlling the operating means. In a preferred embodiment, the device includes a pair of opposed straps, attached to a healthy, small-diameter donor blood vessel such as a femoral artery in the leg. The straps are displaced from each other over a period of time to continuously distend or elongate the donor vessel. The distended portion of the donor vessel is excised at the time of the bypass surgery. The ends of the donor vessel are then sutured end to end to repair the donor vessel, a procedure common in vascular repair and generally accomplished without complication. The result is a totally autologous, living vascular graft.

32 Claims, 5 Drawing Sheets

OTHER PUBLICATIONS

Kanda, et al., "Phenotypic reversion of smooth muscle cells in hybrid vascular prostheses," *Cell Transplant*. 4(6):587–95 (1995).

Leung, et al., "Cyclic stretching stimulates synthesis of matrix components by arterial smooth muscle cells in vitro," *Science*. 191(4226,:475–77 (1976).

Ruiz–Razura, et al., "Acute Intraoperative arterial elongation: Histologic, morphologic, and vascular reactivity studies," *J. Reconstructive Microsurgery*, 10(6):367–73 (1994).

Stark, et al., "Rapid elongation of arteries and veins in rats with a tissue expander," *Plastic and Reconstructive Surgery*, 80(4):570–78 (1987).

\* cited by examiner

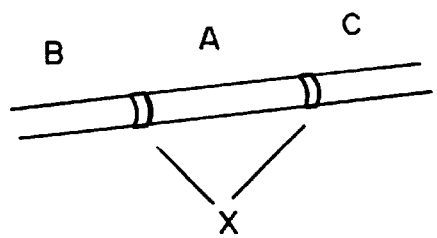
FIG. 4A
FIG. 4B
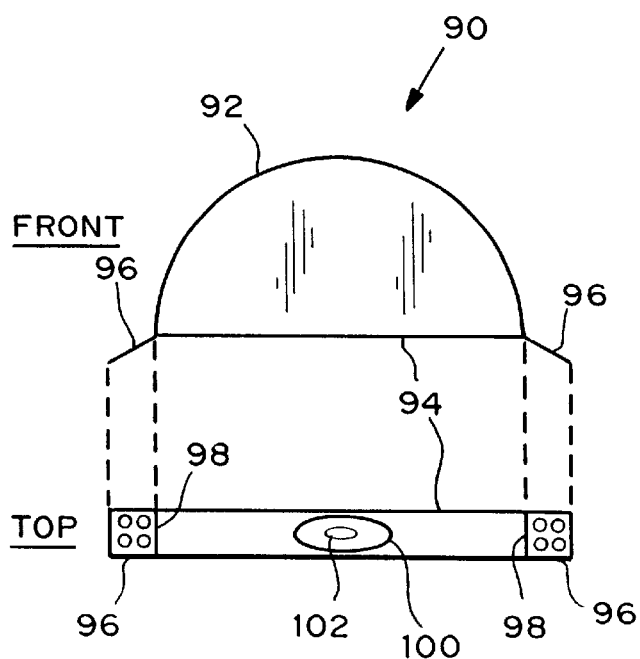
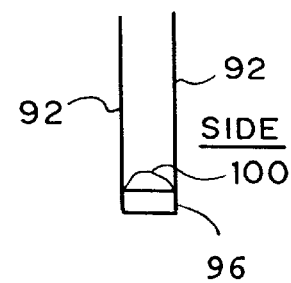
FIG. 5A
FIG. 5B

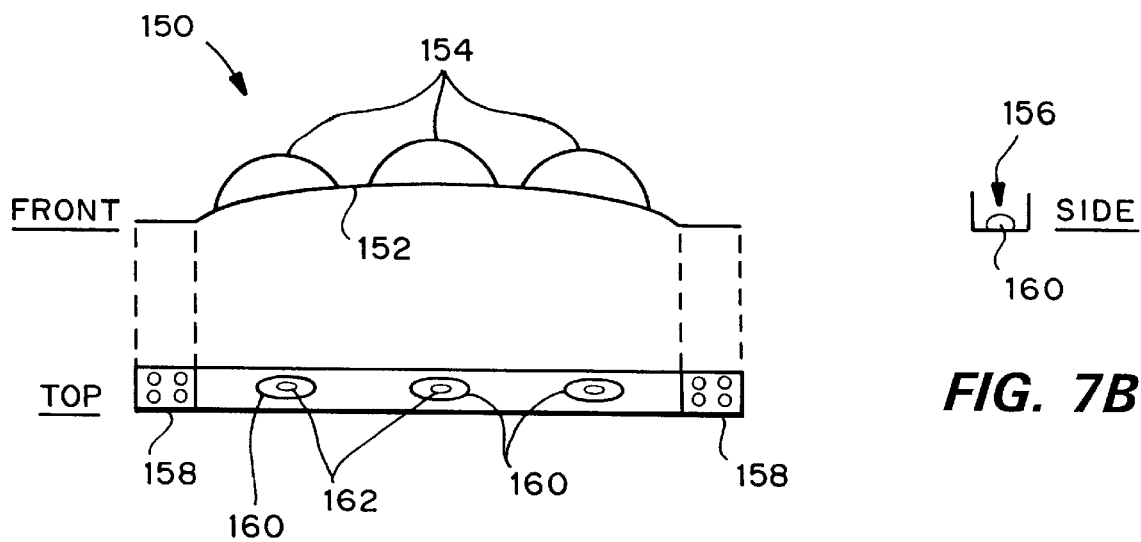
FIG. 7A
FIG. 7B
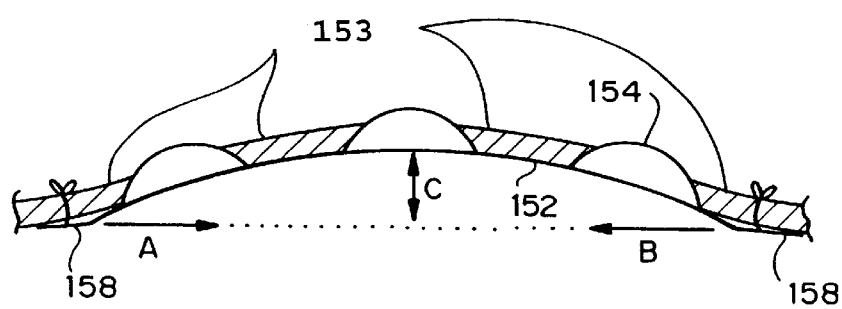
FIG. 8A
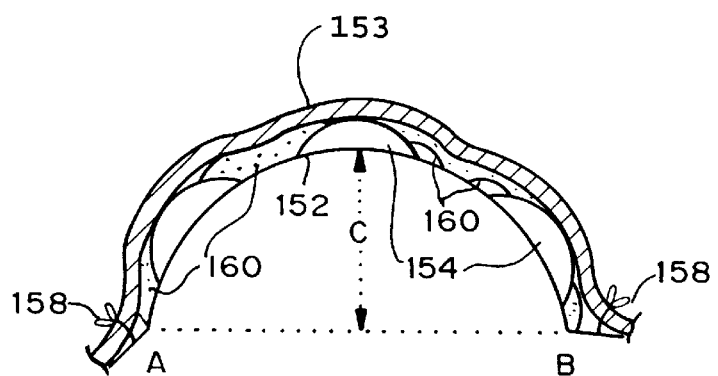
FIG. 8B

AUTOLOGOUS VASCULAR GRAFTS CREATED BY VESSEL DISTENSION

CROSS-REFERENCE TO RELATED APPLICATIONS

Priority is claimed to U.S. provisional application Serial No. 60/087,027, filed May 28, 1998.

STATEMENT REGARDING FEDERALLY SPONSORED RESEARCH

Not applicable.

BACKGROUND OF THE INVENTION

The present invention is generally in the area of methods and devices to obtain vascular tissue grafts and more specifically in the area of methods and devices to obtain autologous grafts prepared from living vascular tissue.

Vascular grafts are commonly used by surgeons to bypass obstructions to blood flow caused by the presence of atherosclerotic plaques. Vascular grafts also are used to treat other vascular problems. Grafts for bypass are often, but not exclusively, used in the coronary arteries, the arteries that supply blood to the heart. The materials used to construct a vascular graft usually are either synthetic or of biological origin, but combinations of synthetic and biological materials are also under development. The most successful biological vascular grafts are autologous saphenous vein or mammary artery. Some common synthetic grafts are made of polytetrafluoroethylene (PTFE) (GORTEX™) or polyester (DACRON™). Autologous grafts have generally been used more successfully than synthetic grafts. Autologous grafts remain patent (functional) much longer than synthetic grafts, but saphenous veins are seldom functional more than five years. The short lifetime of synthetic grafts is especially evident with small diameter grafts, as most small diameter synthetic grafts occlude within one to two years.

Mammary artery is the autologous graft of choice, because it typically has a longer life than venous grafts (95% patent at 5 years versus 85% patent at 2 years). Mammary arterial tissue, however, is difficult to harvest and typically is not available in lengths sufficient for effective bypass. Moreover, obtaining sufficient venous tissue for repairing an occluded artery is problematic.

In some cases, autologous or homologous saphenous vein preserved by freezing or other processes is used.

With people living longer, multiple surgeries are more common. At the same time, open heart surgery is becoming more routine, aided by the development of new, minimally invasive procedures which have dramatically simplified the surgery and reduced the recovery time. Development of a longer lasting small-diameter vascular graft is the subject of much academic and industrial research. One current approach is to combine cell culture and biomaterials technologies to make a living, "tissue engineered" graft. This effort, however, is hindered by the requirements of a successful graft: it should be self-repairing, non-immunogenic, non-toxic, and non-thrombogenic. The graft also should have a compliance comparable to the artery being repaired, be easily sutured by a surgeon, and not require any special techniques or handling procedures. Grafts having these characteristics are difficult to achieve. Despite the substantial effort to date and the potential for significant financial reward, academic and industrial investigators have failed to produce graft materials which have demonstrated efficacy in human testing.

Efforts to avoid or minimize the need for vascular grafts for repair of otherwise healthy vascular tissue have been described. For example, Ruiz-Razura et al., *J. Reconstructive Microsurgery*, 10(6):367–373 (1994) and Stark et al., *Plastic and Reconstructive Surgery*, 80(4):570–578 (1987) disclose the use of a round microvascular tissue expander for acute arterial elongation to examine the effects on the tissue of such acute hyperextension. The expander is a silicone balloon that is placed under the vessel to be elongated. The balloon is filled with saline over a very short period of time, causing acute stretching and elongation of the vessel. The method is purported to be effective for closure of arterial defects up to 30 mm without the need for a vein graft. These techniques are appropriate for trauma, but are not used for restoring blood flow in vessels that are occluded, for example by disease, which are treated by surgically bypassing the obstruction with a graft. The disclosed methods and devices fail to provide an autologous graft or versatile substitute. Moreover, the acute stretching may damage the vessel.

Accordingly, it is an object of the invention to provide a method, and devices therefor, for creating an autologous blood vessel graft.

SUMMARY OF THE INVENTION

A method for creating an autologous vessel graft is provided, wherein vessel distension is used to stimulate growth of a donor vessel for grafting. Devices useful in the method are provided to stretch the vessel rectilinearly, curvilinearly, or in a combination thereof The devices can be implanted, for example using endoscopic techniques, in a bypass surgery patient prior to the bypass surgery, in order to create blood vessel grafts. The distended portion of the donor vessel is excised at the time of the bypass surgery. The ends of the donor vessel are then sutured end to end to repair the donor vessel, a procedure common in vascular repair and generally accomplished without complication. In an alternative embodiment, a section of donor vessel is surgically excised from the bypass surgery patient and then distended in vitro in a medium for cell growth. The result using either approach is a totally autologous, living vascular graft.

The device preferably includes a stretching mechanism which is attached to a donor blood vessel, means for operating the stretching mechanism to cause the vessel to distend, and a controller, preferably externally located, for controlling the operating means. In a preferred embodiment for rectilinear stretching using vessel attachment points that are movable relative to one another, the device includes a pair of opposed straps, which can be attached to a healthy, small-diameter donor blood vessel such as a femoral artery in the leg. The straps are displaced from each other over a period of time to continuously distend or elongate the donor vessel.

In another preferred embodiment, the device includes a stretching mechanism having vessel attachment points that are fixed relative to one another during the stretching operation. For example, the stretching mechanism can include a rigid surface having two opposing flexible ends that are fixedly attached to the donor vessel, and an inflation or expansion means, such as a balloon, disposed between the flexible ends adjacent the rigid surface. The vessel is distended in a curvilinear manner as the inflation or expansion means is inflated or expanded.

In another preferred embodiment, the device includes a stretching mechanism that provides both rectilinear and curvilinear stretching. For example, the stretching mechanism can include a curved or angled surface having two opposing flexible ends that can be fixedly attached to the donor vessel, wherein the ends can be drawn towards one another.

BRIEF DESCRIPTION OF THE DRAWINGS

FIGS. 4a and 4b are an illustration of a normal and stretched blood vessel.

FIGS. 5a and 5b are perspective views of the front (FIG. 5a) and side (FIG. 5b) of a preferred embodiment of the device for vessel distension using fixed points of vessel attachment.

FIGS. 7a and 7b are perspective views of the front (FIG. 7a) and side (FIG. 7b) of a preferred embodiment of the device for both rectilinear and curvilinear vessel distension.

FIGS. 8a and 8b are diagrams showing vessel distension using a preferred embodiment of the device for both rectilinear and curvilinear vessel distension.

DETAILED DESCRIPTION OF THE INVENTION

Figure 1:
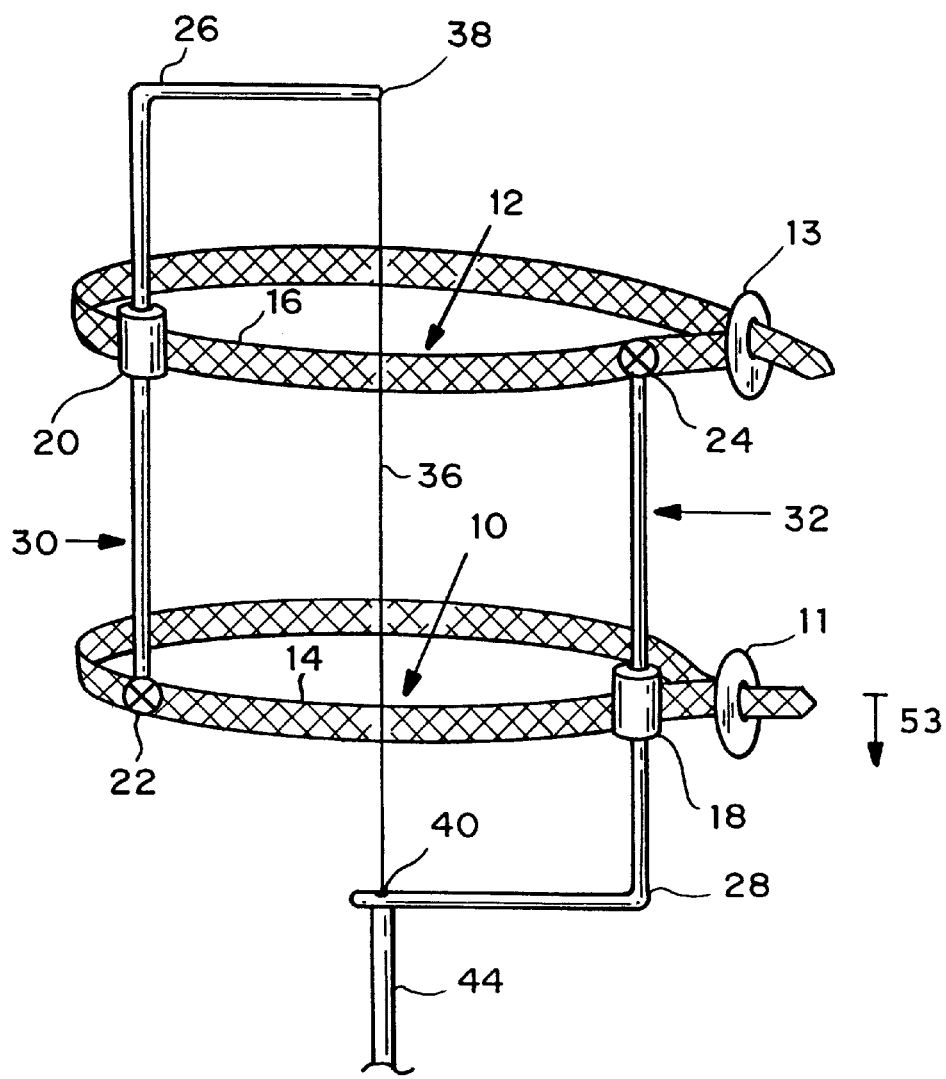
FIG. 1 is a plan view of a preferred embodiment of the device for vessel distension.
Figure 1:
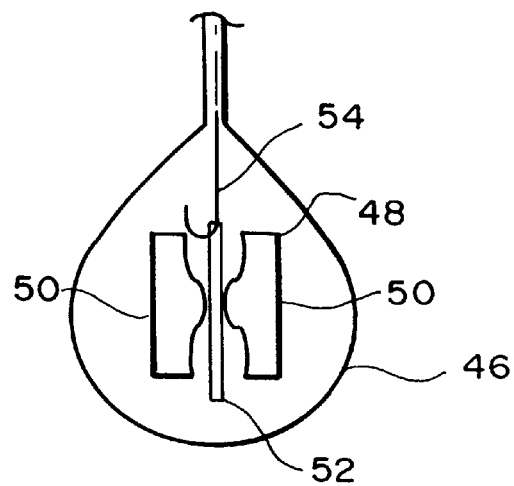

It is known that smooth muscle cells, which dominate the media, the major load bearing layer of the arterial wall, proliferate and increase their production of extracellular matrix in response to mechanical stimulation. It was discovered that this knowledge can be advantageously applied to create an autologous graft of appropriate diameter for coronary bypass or other vascular graft application using a distension device to stimulate angiogenesis. While an autologous graft is preferred, the devices and methods described herein also can be applied to an artery from a transgenic animal genetically engineered to have tissues which will not be rejected by humans. The distension device can be adapted to operate in vivo or in vitro.

Distension Device

The distension device attaches to the donor blood vessel and distends or stretches it to form an elongated portion. Stretching can be continuous, cyclic, or intermittent, and can occur rectilinearly, curvilinearly, or in a combination thereof The stretching can occur between vessel attachment points that are movable relative to one other or in fixed positions relative to one other. The device can also be adapted for use in a process that combines stretching the vessel while the attachment points are fixed relative to each other with stretching the vessel by moving the attachment points away from one another.

I. Movable Attachment Positions

The device includes a stretching mechanism which is attached by means such as straps or sutures to the donor blood vessel, means for operating the stretching mechanism to cause the vessel to distend, and a controller for controlling the operating means.

a Stretching Mechanism

In a preferred embodiment, the distension device stretching mechanism includes a pair of opposed straps or loops that are fixedly attached to the donor blood vessel such as by sutures. The opposed straps are displaced away from each other over a period of time so that the donor vessel elongates as the straps are displaced. After a period of time, such as when the straps are displaced a pre-determined distance, the section of vessel and the device are removed and the ends of the donor vessel are sutured together.

The device straps should be made out of a biocompatible material such as a synthetic or natural polymer or metal. The straps must be able to be attached to the vessel, for example, using sutures, staples, or adhesion. Examples of suitable material for the straps are polytetrafluoroethylene (PTFE), polyester (e.g., DACRON™), nylon (e.g., DELRIN™), polysulfone, polypropylene, and polyethylene. The strap material preferably is doped to render it radio opaque, so that the stretching process can be monitored using x-ray techniques. The straps can be wrapped in a material that is then attached to the vessel, or they can include perforations or holes to accommodate suturing to the vessel. The straps preferably have a flex strength so as to support the distending force applied on the stretching mechanism.

The device includes a means to displace the straps away from each other and stretch the vessel. This displacement can be accomplished by any of a variety of techniques. For example, the device can include rods attached to the straps that can be moved to push or pull on the straps to slowly displace the straps from each other. The rods can be moved, for example, by mechanical or hydraulic means.

b. Operating means

The device includes means to operate the stretching mechanism, preferably including a prime mover and electronic drivers for the prime mover, both of which are preferably implanted. The prime mover can be mechanical, such as a linear-motor which operates the stretching mechanism to push and/or pull the straps away from each other. A rotary motor could also be used to generate the required linear motion, using techniques known in the art. Alternatively, the prime mover can operate hydraulically.

Linear or rotary piezo micro-motor devices (actuators) deliver small step sizes, small forces, have relatively simple control electronics and inherent force overload protection. Suitable devices are available from a number of vendors, including Micro Pulse Systems, Inc. Parameters of the operating means include the force applied by the stretching mechanism, the rate and direction of movement of the stretching mechanism, the length of time that the stretching mechanism is operated, and the type of stretching applied, i.e. continuous, cyclic, or intermittent.

c. Controller

The controller controls the operating means. In the in vivo distension embodiments, the controller can include a microprocessor that is implanted and that can be activated, programmed, or reprogrammed by an externally applied magnetic or electromagnetic field. The controller also can be activated, programmed, or reprogrammed externally using wires that pass through the skin.

A preferred embodiment of the device is shown in FIG. 1. Proximal locking strap 10 and distal locking strap 12 are of adjustable length appropriate for a good fit around the donor blood vessel to be distended. Blood vessels range from about 0.2 to 2 cm in diameter. The locking straps 10, 12, include a lace 14, 16, respectively, of a bio-compatible material, such as DACRON™, that can be secured to the donor vessel, such as by suturing, stapling, or using an adhesive agent. In a preferred embodiment, the laces are designed similarly to the sewing rings of a standard artificial heart valve. Alternatively, a layer of a material, such as a fabric or film, can be attached to the strap so that the vessel can be sutured, stapled, or adhered to the material to hold the strap to the vessel. In another embodiment, the strap includes perforations, holes, or other structural features amenable to suturing or stapling, so that the vessel can be sutured or stapled directly to the strap. The locking straps have a head 11, 13 with an internal aperture. Preferably, the straps 10, 12 include a plurality of teeth (not shown) that, when the free end of the lace 14, 16 is inserted through the aperture of the head of the strap, engages the head and prevent the free end of the lace from becoming disengaged, in a manner similar to that of standard pull-ties. Alternatively, the head of the strap can engage the strap if the lace 14, 16 does not cover the entire strap or if the strap includes securing holes or perforations as described above.

Sliding bearings 18, 20, on straps 10, 12, respectively, and stops 22 and 24, respectively, can be either attached to or integrally formed (during manufacture) with the straps or laces as shown. The bearings and stops are preferably made of the same material as the straps, although other biocompatible materials can be used.

A first push/pull rod 26 is fixedly attached to proximal tie strap 10 at stop 22. A second push/pull rod 28 is fixedly attached to distal tie strap 12 at stop 24. The two push/pull rods are preferably initially not fitted to the locking straps but are easily assembled on the device in vivo after the locking straps are secured around the vessel and sutured or otherwise fixed in place. The push/pull rods slide through the bearings 18, 20 and engage the stops 22, 24. The proximal locking strap 10 including the lace 14, sliding bearing 18, stop 22, and the fixedly attached rod 26 form a first integrated stretch unit 30. The distal locking strap 12 including the lace 16, sliding bearing 20, stop 24, and the fixedly attached rod 28 form a second integrated stretch unit 32. Push/pull rods 26, 28 are preferably made of a rigid material such as stainless steel or a biocompatible, rigid plastic.

Figure 2:
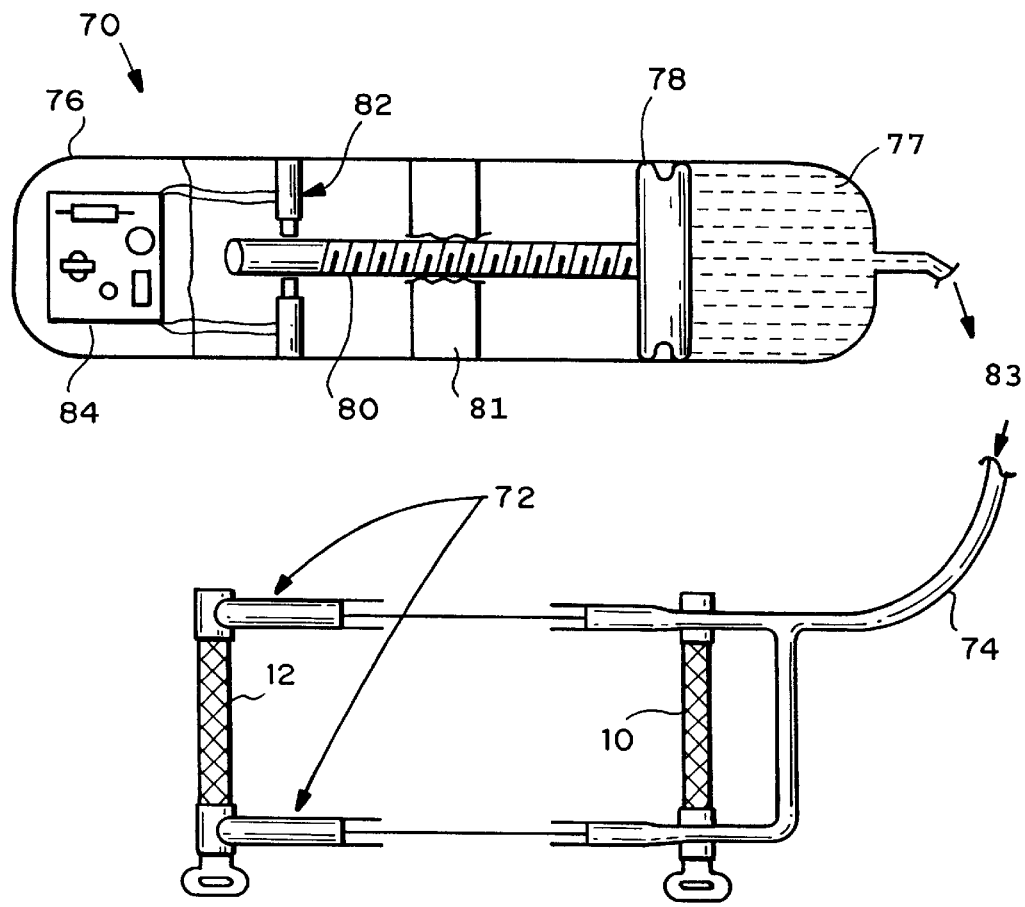
FIG. 2 is a plan view of a second preferred embodiment of the device for vessel distension.

A wire (or cable) 36, preferably stainless steel, is fixedly attached to first push/pull rod 26 at 38 and passes freely through a hole 40 in push/pull rod 28. The wire 36 then passes freely through the sheath 44 into the prime mover housing 46. The prime mover shown is a piezo-actuator or other linear motor. Those skilled in the art will recognize that several suitable means for pulling the wire or cable are known. For example, the wire or cable can be pulled by a hydraulic cylinder or actuator powered by an implanted pump or by transcutaneous injection of a fluid, such as saline. The wire or cable also could be wound on 4 rotating reel or attached to a lead screw configured to produce linear motion, wherein either are powered by electric or hydraulic rotary actuators. FIGS. 1 and 2 show two opposing piezo-actuators 50 contained in the housing 46 which can be activated to provide micron-sized step advancement of the driven element 53. Wire 36 is attached to driven element 53 by a hook 54 or other means so that wire 36 is advanced along with driven element 52. Micro Pulse Systems, Inc. makes micro-actuators that are suitable for the device disclosed herein.

As the actuator 48 pulls the wire 36, the first integrated stretch unit 30 is pushed/pulled towards the actuator 48, in the direction of arrow 52. The locking straps are thus displaced away from each other.

The device preferably includes an external driver and controller, which are not shown in the Figures. In a preferred embodiment, the cable can be activated from outside the body once the cable is passed through the skin. Mechanisms outside the body are easier to design and transcutaneous catheters and similar conduits are highly developed.

FIG. 2 illustrates a second preferred embodiment 70 of a device for vessel distension. The hydraulic embodiment uses two miniature, double-acting hydraulic cylinders 72, for example made of stainless steel or polymer, through which hydraulic force is exerted to stretch the blood vessel by pushing on strap 10. Double acting hydraulic cylinders 72 are connected by a hydraulic line 74 into which fluid flows to the housing 76 which is a reservoir of a fluid such as saline 77. Pressure is generated by a piston 78 driven by threaded rod 80 positioned in a rod support 81 pushing the saline from the reservoir out at 83, but may also be generated by means external to the body using a catheter through the skin. The threaded rod 80 is driven using torque generated by frictional engagement with piezo-actuators 82 or by a miniature permanent magnet or other suitable motor. Micro Pulse Systems Inc. supplies piezo-actuators suitable for use in the device. Driver electronics and a power source are indicated by 84. Note that while FIG. 2 shows a hydraulic mechanism wherein only strap 10 is moved, the hydraulic system may be readily adapted by one of skill in the art to exert force on both strap 10 and strap 12.

The mechanical or hydraulic stretching mechanism works to move the straps apart slowly over a period of time of up to several weeks. In one embodiment, the driver may be pre-programmed to operate autonomously, or the driver may be programmed (or reprogrammed) following implantation by transcutaneous electromagnetic means, based, for example, on x-ray data or other indications of how the process is proceeding. The driver may be simply turned on or off, or may be programmed or reprogrammed by a magnetic field sensing device such as a reed switch (relay) or by other electronic devices or circuits responsive to magnetic or electromagnetic fields. The field is generated by using the external driver control to periodically activate an external source positioned so as to activate the electronic driver circuit. The external driver control may be pre-programmed to provide a stretch of several centimeters over about one month. Alternatively, cyclic stretching of increasing peak and mean amplitude may be used. Using piezo actuators, activating the driver can produce incremental movements of the mechanical or hydraulic stretching mechanism as small as a few microns. The prime mover is designed to be force limited so as to preclude over-stretching the vessel. Force limitation is inherent if the piezoelectric actuators are used in either embodiment and, in the case of permanent magnetic motors, can be designed into the electronic driver circuit.

II. Fixed Attachment Positions

In stretching an artery to stimulate angiogenesis, the blood vessel portion that is beyond the region where the stretching apparatus is attached will be relaxed from its normal stretched state and could possibly be relaxed to the point where it is put in compression, as illustrated in the FIGS. 4a and 4b. FIG. 4a shows a blood vessel as it is normally stretched in vivo, and FIG. 4b shows how a stretching device having points of contact (X) between vessel sections A and B and between A and C. The stretching device elongates section A while relaxing sections B and C. The consequences of this are unknown, but can be avoided if the blood vessel is stretched between two fixed points, as described herein.

The fixed point device is described with reference to a preferred embodiment shown in FIGS. 5a and 5b. The device 90 includes two semicircular or similarly shaped thin, yet rigid, plates 92 made of or completely covered by a biocompatable material, such as stainless steel, fiber composite, or polymer. The plates are separated and connected so as to remain parallel by a flat rectangular strip of similar material 94. The ends of the strip 96 are perforated or otherwise formed to accept surgical sutures or other means (e.g., adhesive) known in the art to secure a blood vessel to the strip at its ends. The ends 96 are also flexible and easily bent, but without breaking, about axis 98 shown. The device can be formed from a single appropriately shaped thin plate. The area between the plates contains at least one inflatable balloon 100, which may be formed from silicone, rubber, elastomeric polymers, or any other highly deformable biocompatible material. As the balloon is inflated, it fills the space between the two thin plates without significantly changing the spacing between the two plates, since the plates and strip are sufficiently rigid to ensure this. Inflation of the balloon can be accomplished using at least one access port 102, through which a fluid, such as saline, is injected, for example, through a needle or catheter connected to a syringe or similarly functioning device. The inflation process can occur through the skin. The balloon is designed and attached to the strip in such a manner that, at full inflation, it assumes more or less the shape of the space between the two plates confining it.

An alternative stretching mechanism is provided by hydrophilic or chemically reactive synthetic substances (e.g., various polymers) or other natural materials (e.g., cellulose) known to significantly expand their dry volume when activated as by exposure to fluid or possibly other stimuli (e.g., heat, radiation or various chemical agents). Such materials are available in foamed, fiber or other forms, any of which may be adapted by one of skill in the art to effect the balloon inflation described herein. One or more of these materials can be placed inside the balloon and expanded by the controlled addition of a fluid or chemical agent, such as by injection into the balloon, which causes the materials to expand, inflating the balloon, in much the same way as simply pumping saline or another fluid into the balloon as described above. The material could also be otherwise encapsulated or separated from the stimuli so as to control its means and rate of activation. For example, expandable material could be provided with a degradable coating or other timed-release mechanism, such can be adapted from those used in controlled drug delivery. Alternatively, the balloon can be omitted, and the hydrophilic or other volume expanding material can simply be placed between the two plates in such a manner that exposure to body fluids or another appropriate stimulus causes the material to expand and fill the area between plates.

III. Combination Fixed/Movable Attachment Positions

An alternative embodiment combines rectilinear and curvilinear stretching. A preferred embodiment is a slightly modified version of device 90 shown in FIG. 5. The modified device is shown in FIGS. 7a and 7b. The device 150 includes strip 152, that is formed much like strip 94, except that it is formed in a slightly curved or angled configuration and includes at least one, and preferably several, tabs 154, positioned at or near the edge of the strip, so as to form a channel 156. Strip 152 has flexible ends 158 for attachment to the vessel.

A vessel, preferably an artery, is placed in channel 156 and attached to the strip 152, as for example described for strip 94, wherein plates 154 serve to hold the vessel in place. The area between the plates contains at least one inflatable balloon 160, like balloon 100 described above. Inflation of the balloon(s) can be accomplished using at least one access port 162, also as described above.

Method for Distending a Blood Vessel

The distension device can be adapted to operate in vivo or in vitro, that is to distend a portion of a blood vessel in vivo or following its excision from the body and subsequent placement in a medium for cell growth. As used herein, the phrase "medium for cell growth" includes any in vitro system for facilitating cell division and growth of vessel tissue. For example, the distension device can be attached to an excised portion of donor vessel and submerged in a medium for cell growth in a temperature controlled container. As described in Example 1 below, it has been shown that distension in an organ culture (bio-reactor) significantly stimulates cell division, and can be simple to control. See, for example, U.S. Pat. No. 5,899,936 to Goldstein; U.S. Pat. No. 5,879,875, to Wiggins, et al., and U.S. Pat. No. 5,888,720 to Mitrani, which describe techniques for organ and tissue culture which can be adapted to the methods described herein.

I. Operating the Movable Positions Device

The method for distending a donor blood vessel includes attaching a stretching mechanism to the donor vessel and operating the stretching mechanism to stretch the donor vessel. Preferably, the method involves using a device wherein a pair of straps are fixedly attached to the donor vessel and moved away from one another so that the portion of the vessel between the straps is distended. The distended portion can then be excised and used as a graft. Total distensions typically are about 4 to about 6 cm per bypass. The rate of vessel distension can readily be optimized by those of skill in the art. Distension rates can be linear or nonlinear, and may average, for example, about 1 mm/day.

Figure 3:
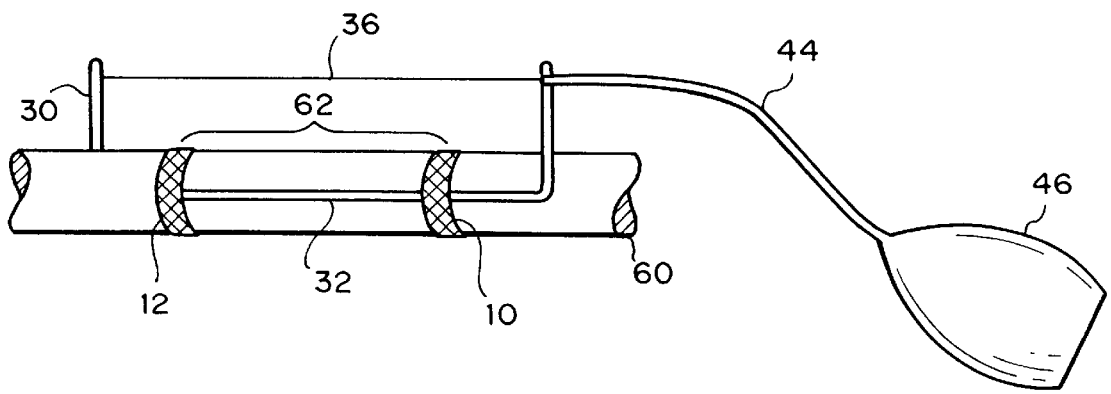
FIG. 3 is a side elevational view of the distension device shown attached to a donor blood vessel.

A preferred embodiment of the method is illustrated in FIG. 3, wherein a device is attached to a donor blood vessel 60. The device can be assembled prior to or at the time of implantation. Straps 10, 12 are engaged so as to encircle the donor vessel and are then sutured in place. Push/pull rods 30, 32 are attached to the straps. Wire 36, and the housing assembly shaft 44, housing 46 and actuator 48 are attached to the device. The prime mover is implanted complete with its drive circuit and a minimal power source. As the device is operated, the section of vessel 60 between the straps 10, 12, indicated by 62, stretches.

II. Operating the Fixed Positions Device

Figure 6A:
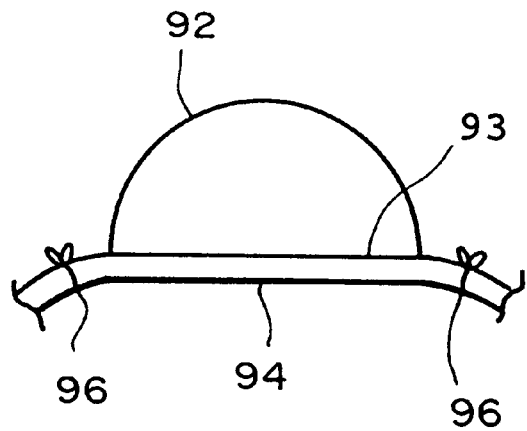
FIGS. 6a–6c are diagrams showing vessel distension using a preferred embodiment of the device having points of vessel attachment that are fixed relative to one another.
Figure 6B:
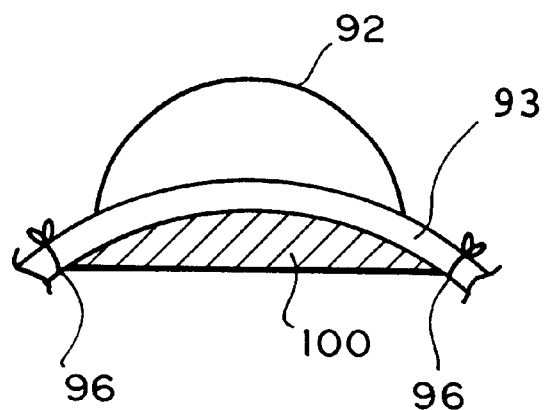
Figure 6C:
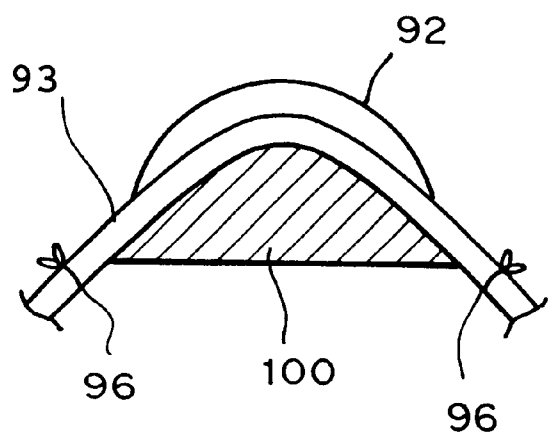

The device using fixed attachment positions is preferably operated as shown in FIGS. 6a–6c. FIGS. 6a–6c show a cross-sectional view (a—a) of the device in FIG. 5, at increasing degrees of vessel distension occurring with increasing inflation/expansion of the balloon/expanding material. In operation, the target blood vessel 93 is placed between the two plates 92, resting on the uninflated balloon or unexpanded material 100 and secured to the flexible ends 96 of the strip, for example by sutures or other suitable means (FIG. 6a). As the balloon is inflated (or the material expanded), the blood vessel 93 is stretched, between the two fixed ends 96 and continues to stretch as the space between the two plates is filled (FIGS. 6b and 6c), without the possibility of reducing the tension in or compressing the blood vessel 93 not between the points of attachment.

III. Operating the Combination Fixed/Movable Positions Device

The device using the combination of fixed and movable attachment positions is preferably operated as shown in FIGS. 8a–8b. FIG. 8a shows a blood vessel attached to the device before application of the bending force (i.e. before distension). FIG. 8b shows the device and vessel following application of the bending force, wherein strip end A is drawn towards strip end B.

In operation, the target blood vessel 153 is first placed between plates 154, resting on the uninflated balloon or unexpanded material 160 and secured to the flexible ends 158 of the strip, for example by sutures or other suitable means. The ends 158 of the strip 152 are then drawn towards each other by mechanical or other forces so as to cause strip 152 to bend or flex, thereby stretching the vessel 153. The ends can be drawn towards one another by any suitable means, including a mechanical or magnetic force, or by a differential expansion effect, for example where the strip consists of laminants of materials that contract or expand differently from one another when exposed to a stimulus, such as heat (thermal expansion) or water (e.g., top layer of strip hydrophilic while bottom layer hydrophobic). The mechanical means can include, for example, the linear or rotary piezo micro-motor devices described herein. As the strip 152 is bent, distance C increases and distance AB decreases, causing the section beyond either A or B to be stretched in a rectilinear manner.

Additionally, balloon 160 is inflated (or the material expanded), the blood vessel is stretched, between the two ends 158 and continues to stretch as the space between the two plates is filled. Thus, the section of blood vessel between ends A and B is stretched in a curvilinear manner. The two modes of stretching can occur simultaneously, one after another in either order, or any combination thereof.

Application of the Distension Devices and Methods

In a preferred embodiment of the in vivo distension method, the device is implanted in the patient and vessel distension effected over a period of time. Then the site of implantation is re-exposed, all or a portion of the vessel section (identified as 62 in FIG. 3) is removed, the device is removed, and the free ends of the donor vessel are sutured to each other. The removed section is then ready for use as a graft in the patient.

In a preferred embodiment of the in vitro distension method, a portion of donor blood vessel (e.g. shorter than that needed for a graft) is surgically excised from the patient in need of the graft, and then the vessel portion is distended over a period of time. All or a portion of the distended vessel is then ready for use as a graft in the patient.

The devices and methods of use thereof described herein are further described by the following non-limiting example.

Example 1
In Vivo Vessel Stretching to Stimulate Cell Division

Leung et al., *Science* 191:475–77 (1976) showed that cyclic stretching stimulates synthesis of matrix components in arterial smooth muscle cells in-vitro. Subsequent studies in arterial tissue have been limited to the effects stretching on cells attached to a membrane in cell culture (see, for example, Birukov, et al., *Molecular & Cellular Biochem.* 144:131–39 (1995); Costa, et al., *FASEB J.* 5:A1609–7191 (1991)) or in a vascular graft construct (Kanda, et al., *Cell Transplantation* 4(6):587–95 (1995)). No known studies, however, have analyzed the effect of stretch on cells in intact vessel walls. Therefore, a study was made of porcine carotid arteries in an organ culture system developed by Conklin (Conklin, B. *Viability of Porcine Common Carotid Arteries in a Novel Organ Culture System* MS Thesis, Georgia Institute of Technology, 1997), in order to determine the effect of axial stretching on smooth muscle cell division in an intact vessel.

Left and right external carotid arteries were obtained at slaughter, one for testing and the other serving as a control. Both vessels were immersed in cell culture media containing DMEM (Sigma D1152), sodium bicarbonate (3.7 g/L, Sigma), L-glutamine (2 mM, Sigma), antibiotic-antimycotic solution (10 ml/L, Gibco), and calf serum (CS 10%, Integren). The vessels were perfused with the same media with the addition of Dextran (5% by weight, MW 282,000 Sigma). The test and control specimen both were maintained at body temperature and subjected to pulsatile flow in the physiological range. The control specimen was restored to and maintained at the in-vivo length, which corresponds to a stretch ratio of 1.5, for the duration of the experiment. The test specimen was stretched an additional 30% to a stretch ratio of 1.8 over the first two and one-half days of the five day experiment.

Bromodeoxyuridine ("BRDU") staining was used to compare the number of cells which were dividing in the test and control specimens. On the fifth day, the specimens were pressure-fixed with formalin and histologic slides prepared for cell counting using light microscopy. The BRDU was added on day four and the test specimen showed that 6.8+/−2.8% of the cells were dividing, while only 3.08+/−2.9% of the cells were dividing in the control specimen. The results clearly suggest that axial stretching can be used to enhance cell division in blood vessels, and should therefore be useful in the growing vessel segments for use in creating blood vessel grafts.

Modifications and variations of the present invention will be obvious to those of skill in the art from the foregoing detailed description. Such modifications and variations are intended to come within the scope of the following claims.

I claim:

1. A device for distending a donor blood vessel of a human or animal in need thereof, comprising:
   a stretching mechanism attachable directly to the donor blood vessel; and
   means for operating the stretching mechanism to cause the vessel to extend axially.

2. The device of claim 1 wherein the stretching mechanism can stretch the vessel rectilinearly, curvilinearly, or in a combination thereof.

3. The device of claim 2 wherein the means for stretching the vessel rectilinearly, curvilinearly, or in a combination thereof, can be operated simultaneously or one after another in either order.

4. The device of claim 1 wherein the stretching mechanism comprises a pair of opposed straps that can be fixedly attached to the donor vessel and moved away from each other over a period of time.

5. The device of claim 3 wherein the means for operating the stretching mechanism comprises a prime mover that is electronically or hydraulically driven.

6. The device of claim 4 wherein the stretching mechanism further comprises a pair of push/pull rods each connected to the opposing straps.

7. The device of claim 1 wherein the stretching mechanism comprises
   a rigid surface having two opposing flexible ends that can be fixedly attached to the donor vessel, and
   an inflation or expansion means disposed between the flexible ends and adjacent to the rigid surface.

8. The device of claim 7 wherein the inflation means comprises a balloon.

9. The device of claim 7 further comprising a pair of plates projecting from the rigid surface, wherein the plates are substantially parallel to each other between the flexible ends, so that the inflation or expansion means is disposed between the plates.

10. The device of claim 1 wherein the stretching mechanism comprises
    a curved or angled surface having two opposing flexible ends that can be fixedly attached to the donor vessel, wherein the ends can be drawn towards one another.

11. The device of claim 10 further comprising a plurality of tabs projecting from the surface so as to form a channel for holding a vessel.

12. The device of claim 1 wherein all or a portion of the device is radioopaque.

13. The device of claim 1 further comprising a controller for controlling the operating means.

14. The device of claim 1 wherein the means for operating the stretching mechanism can operate in an intermittent manner.

15. The device of claim 1 wherein the means for operating the stretching mechanism can operate in a continuous manner.

16. The device of claim 1 wherein the means for operating the stretching mechanism can operate in an cyclic manner.

17. A method for distending a donor blood vessel of a human or animal in need thereof, comprising the steps:

attaching a stretching mechanism directly to the donor vessel; and operating the stretching mechanism to stretch the donor vessel over a period of time.

18. The method of claim 17 wherein the stretching occurs in vivo.

19. The method of claim 17 wherein the donor vessel is excised from the human or animal before attachment of the stretching mechanism.

20. The method of claim 17 wherein the vessel is stretched rectilinearly, curvilinearly, or in a combination thereof.

21. The method of claim 20 wherein the vessel is stretched rectilinearly, curvilinearly, or in a combination thereof, simultaneously or one after another in either order.

22. The method of claim 17 wherein the stretching mechanism comprises a pair of straps that are fixedly attached to the donor vessel and moved away from each other so that the portion of the vessel between the straps is distended.

23. The method of claim 17 wherein the stretching mechanism comprises a rigid surface having two opposing flexible ends that are fixedly attached to the donor vessel and an inflation or expansion means disposed between the flexible ends adjacent the rigid surface, and wherein the inflation or expansion means is inflated or expanded so that the portion of the vessel between the flexible ends is distended.

24. The method of claim 17 wherein the stretching mechanism comprises a curved or angled surface having two opposing flexible ends that are fixedly attached to the donor vessel, and wherein the ends are drawn towards one another so that the portion of the vessel between the flexible ends is distended.

25. The method of claim 17 wherein the stretching mechanism is operated in an intermittent manner.

26. The method of claim 17 wherein the stretching mechanism is operated in a continuous manner.

27. The method of claim 12 wherein the stretching mechanism is operated in an cyclic manner.

28. A method of forming an autologous vascular graft in a human or animal in need thereof, comprising:

(a) distending a donor blood vessel by use of a method comprising
   (i) attaching a stretching mechanism directly to the donor vessel, and
   (ii) operating the stretching mechanism gradually or repeatedly over a period of time sufficient to stretch the donor vessel to a desired length;

(b) excising the distended portion of the donor vessel; and (c) suturing the ends of the donor vessel to repair the donor vessel.

29. The method of claim 28 wherein the device or a portion thereof is radioopaque, further comprising taking an x-ray to determine the extent of stretching.

30. The method of claim 28 wherein the device comprises a microprocessor comprising programming the microprocessor to control the stretching.

31. A method of forming an autologous vascular graft for a human or animal in need thereof, comprising:

(a) excising a donor vessel portion of a blood vessel from the human or animal; and (b) distending the donor vessel by use of a method comprising
   (i) attaching a stretching mechanism directly to the donor vessel, and
   (ii) operating the stretching mechanism gradually or repeatedly over a period of time sufficient to stretch the donor vessel to a desired length.

32. The method of claim 31 wherein the distending occurs in a medium for cell growth.

* * * * *

UNITED STATES PATENT AND TRADEMARK OFFICE
CERTIFICATE OF CORRECTION

PATENT NO. : 6,322,553 B1
DATED : November 27, 2001
INVENTOR(S) : Vito

Page 1 of 1

It is certified that error appears in the above-identified patent and that said Letters Patent is hereby corrected as shown below:

Title page,
Item [56], References Cited, add:
-- 4,978,348    12/1990    Ilizarov.
COHEN, et al., "Acute Intraoperative Arterial Lengthening for Closure of Large Vascular Gaps," *Plastic and Reconstructive Surgery*, pp 463-468 (1992).
FU, et al., "Biorheological Features of Some Soft Tissues under a Surgical Tissue Expansion Procedure," *Biorheological Study on Tissue Expansion*, 34:281-293 (1997).
IPPOLITO, et al. "Histology and Ultrastructure of Arteries, Veins, and Peripheral Nerves During Limb Lengthening," *Clinical Orthopaedics and Related Research*, 308: 54-63 (1994).
KOLPAKOV, et al., "Effect of Mechanical Forces on Growth and Matrix Protein Synthesis in the Vitro Pulmonary Artery," *Circulation Research*, 77: 823-831 (1995).
MOORE, et al., "A Device for Subjecting Vascular Endothelial Cells to Both Fluid Shear Stress and Circumferential Cyclic Stretch," *Annals of Biomedical Engineering*, 22: 416-422 (1994).
RUIZ-RAZURA, et al., "Clinical Applications of Acute Intraoperative Arterial Elongation," *J. Reconstructive Microsurgery*, 9: 335-340 (1993).
RUIZ-RAZURA, et al., "Tissue Expanders in Microvascular Surgery Acute Intraoperative Arterial Elongation," *Surgical Forum*, pp. 610-614 (1989). --.

Column 3,
Line 65, delete "a Stretching" and insert -- a. Stretching --.

Column 12,
Line 9, delete "12" and insert -- 17 --.

Signed and Sealed this

Thirteenth Day of August, 2002

Attest:

Attesting Officer

JAMES E. ROGAN
*Director of the United States Patent and Trademark Office*